United States Patent [19]
Campbell

[11] Patent Number: 4,928,710

[45] **Date of Patent: * May 29, 1990**

[54] BREATHING MOUTHPIECE FOR A SNORKEL

[75] Inventor: Steven M. Campbell, Laguna Beach, Calif.

[73] Assignee: U.S. Divers Company, Inc., Santa Ana, Calif.

[ * ] Notice: The portion of the term of this patent subsequent to Sep. 5, 2006 has been disclaimed.

[21] Appl. No.: 255,595

[22] Filed: Oct. 11, 1988

Related U.S. Application Data

[63] Continuation-in-part of Ser. No. 106,388, Oct. 9, 1987, Pat. No. 4,862,903.

[51] Int. Cl.[5] ............................................ A61F 5/56

[52] U.S. Cl. ............................ 128/861; 128/200.29; 128/201.11; 128/206.24

[58] Field of Search .............. 128/861, 200.29, 201.11, 128/201.26, 202.28, 204.26, 206.29, 207.14

[56] References Cited

U.S. PATENT DOCUMENTS

| | | | |
|---|---|---|---|
| 2,521,084 | 9/1950 | Oberto | 128/206.29 |
| 2,589,504 | 3/1952 | Miller | 128/861 |
| 2,669,988 | 2/1954 | Carpenter | 128/201.11 |
| 2,839,053 | 6/1958 | Lorenz | 128/206.29 |
| 3,107,667 | 10/1963 | Moore | 128/861 |
| 3,126,002 | 3/1964 | Owens | 128/861 |
| 3,467,091 | 9/1969 | Aragona | 128/861 |
| 3,603,306 | 9/1971 | Bonin, Jr. | 128/201.11 |
| 4,304,229 | 12/1981 | Curtin | 128/201.11 |
| 4,664,109 | 5/1987 | Rasocha | 128/201.11 |
| 4,862,903 | 9/1989 | Campbell | 128/861 |

*Primary Examiner*—Max Hindenburg
*Assistant Examiner*—Kevin Pontius
*Attorney, Agent, or Firm*—George F. Bethel; Patience K. Bethel

[57] ABSTRACT

The specification sets forth a mouthpiece for use with a snorkel with or without a purge valve for use in diving. The mouthpiece is attached to a snorkel by a conduit and terminates in upper and lower lip flanges for seating within the upper and lower lips. Extending between the upper and lower lip flanges is an upper plate web that conforms to the palate area of a user's mouth. Within the palate web is an opening toward the frontal area for receipt of user's upper front teeth. The mouthpiece incorporates a lower web that extends along the inner jaw region overlying the inner portion of a user's lower teeth. The lower web can include an opening for receipt of the user's lower front teeth or can be split in its conformation with a gap therebetween formed by two tabs that are rounded at their ends. The entire mouthpiece conforms and holds the snorkel in a user's mouth in a facile manner without the requirement of excessive biting and eliminates prior art lugs or bits.

19 Claims, 3 Drawing Sheets

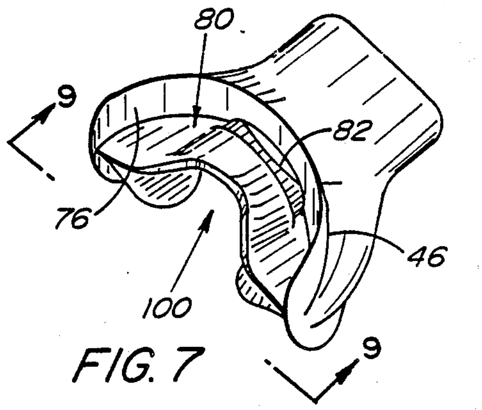
FIG. 7
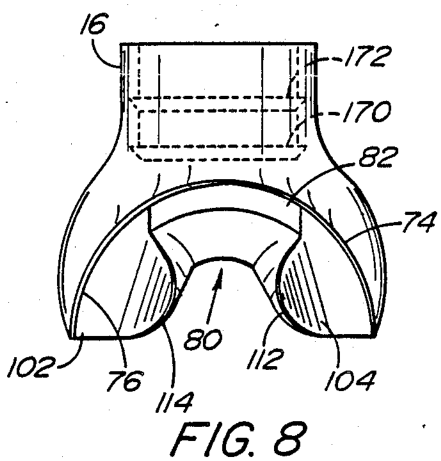
FIG. 8
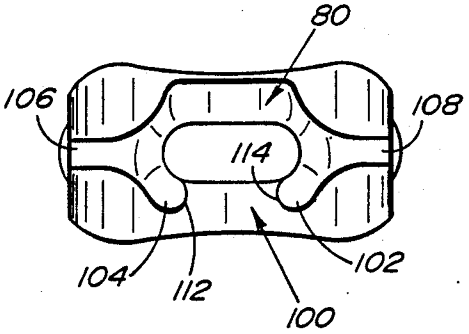
FIG. 9
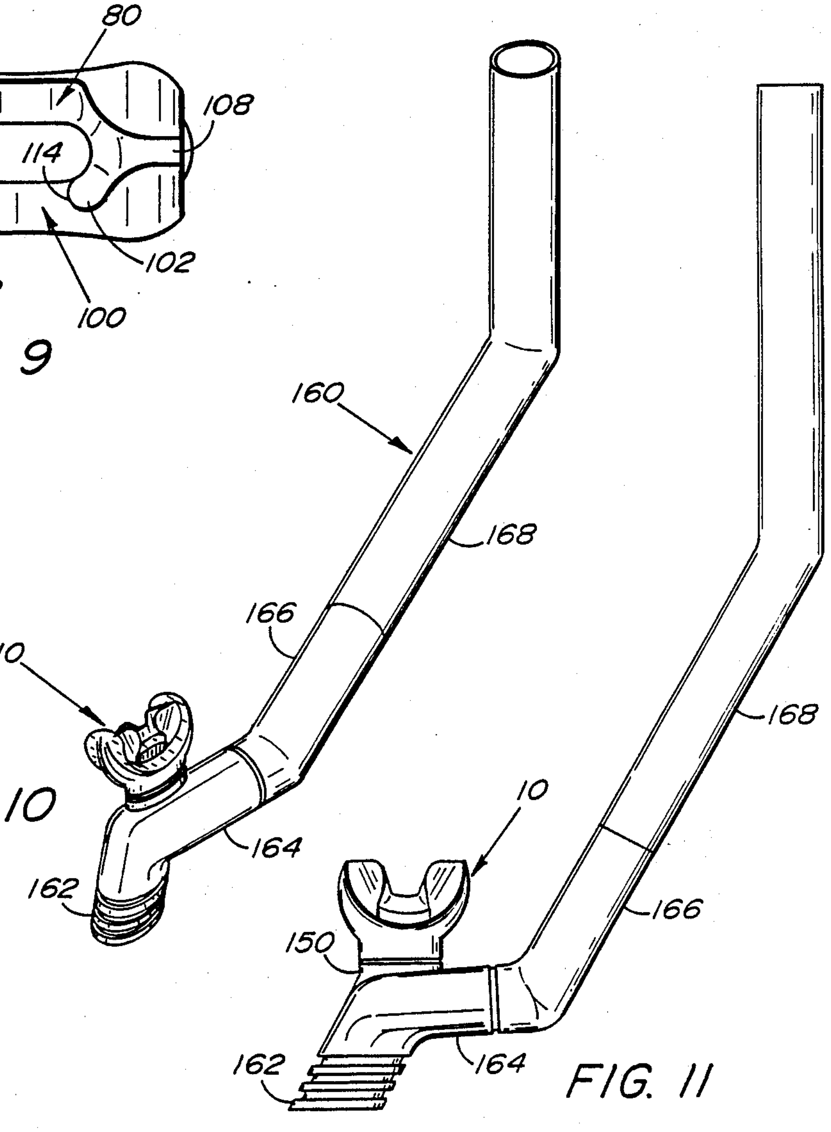
FIG. 10
FIG. 11

BREATHING MOUTHPIECE FOR A SNORKEL

This is a continuation-in-part of application Ser. No. 07/106,388, filed Oct. 9, 1987.

FIELD OF THE INVENTION

The field of this invention lies within the diving art. In particular, it lies within the art of snorkels for divers and mouthpieces pertaining thereto.

BACKGROUND OF THE INVENTION

In all the prior art snorkels, little or no attention has been paid to the mouthpiece. Generally, the mouthpiece follows the standard mouthpiece that has been known over the years. This can be exemplified by the mouthpiece shown in the patent to Bonin, U.S. Pat. No. 3,603,306. In this particular patent there are shown lugs, or biting tabs upon which a user engages the mouthpiece.

An attempt has been made to provide for a more easily held mouthpiece as disclosed in Shamlain's patent, U.S. Pat. No. 3,844,281. This particular patent incorporates the concept of utilizing a conformable thermoplastic material. Thermoplastic material is placed over the lugs or biting tabs that a user normally engages a second stage regulator with. The thermoplastic material is conformably heatset by a user biting into the plastic material when heated.

A further attempt and advance was made by the teaching shown in the Cerniway patent, U.S. Design Pat. No. 246,671. In that patent, the showing was of a second stage regulator mouthpiece. In that case, the entire mouthpiece incorporated a block of thermoplastic material upon which a user could bite down and cause it to conform to the teeth.

In all of the foregoing prior art patents, a solution was not at hand with regard to a comfortable fit of a mouthpiece contoured to the interior surface of a mouth. Also, the facets of the overall requirements for a mouthpiece as demanded in a diver's snorkel were not met.

Fundamentally, the prior art mouthpieces all were nothing other than blocks, tabs, or a bit upon which a user could bite. The end result was that the user had to significantly bite into the mouthpiece w to keep it in place. This became uncomfortable to the user over an extended period of time.

The usage of the Applicant's mouthpiece claimed herein has been shown to be extremely comfortable. Prior art jaw fatigue is substantially decreased. Such jaw fatigue is usually encountered during long durations of diving with conventional mouthpieces.

The snorkel weight is distributed throughout the entire mouth in the Applicant's mouthpiece rather than on two discrete bits or in a densely loaded area. The prior art did not function to remedy this so that a load could be spread over the entire oral, mouth or tooth area, but was rather concentrated.

Another deficiency of the prior art snorkel mouthpieces was that the air flow was not as well oriented as a user would like. The Applicant's invention has been found to provide for easier breathing. This is as a result of being able to provide a further widening to the mouth and opening of the teeth when they engage the snorkel mouthpiece hereof.

The prior art snorkel mouthpieces required that a limited amount of teeth be used to keep the mouthpiece in place. When users who did not have teeth in the right place, used the mouthpiece or had a partial plate or full plate, the grip was not effective by the teeth holding the mouthpiece in place.

The jaw fatigue encountered in prior snorkel mouthpieces created substantial work upon the part of the diver. This has been one of the drawbacks of prior art mouthpieces as they have been used.

The prior art snorkel mouthpieces required a substantial gripping by the mouth to have it close down upon the bits or tabs of the mouthpiece. The invention hereof does not require such action.

In general, the novel snorkel mouthpiece of the invention provides for the snorkel weight to be distributed over a broader area of the entire mouth instead of merely two points. In addition to the foregoing, a user need not bite on the snorkel mouthpiece to keep it in place in a vigorous manner as in the prior art. This also eliminates the likelihood that the user will bite through the snorkel mouthpiece as in prior art mouthpieces.

The end result is that jaw fatigue is limited by the invention hereof and the snorkel mouthpiece provides optimum comfort by resting on the palate areas as well as on the teeth.

The snorkel mouthpiece is held more rigidly in place, which makes it difficult to knock out or fall out as is the case with prior art mouth pieces.

The snorkel mouthpiece can be coupled to or integrally molded with a snorkel to provide an improved snorkel in conjunction with the improved mouthpiece.

The snorkel mouthpiece can be used with snorkels provided with or without a purge valve.

As a consequence, this invention is a step over the prior art and will be seen hereinafter as being a significant aid to divers using snorkels.

SUMMARY OF THE INVENTION

In summation, this invention provides for an improved snorkel mouthpiece having contours and openings which provide for a snorkel being supported in the mouth of a user in a more facile manner.

The invention comprises a mouthpiece for a snorkel having contours to fit the interior of the oral cavity. The fitting of a snorkel mouthpiece on the interior of the oral cavity is enhanced by a graduated upper surface web being angled to fit the upper palate of a user. Compared to the upper web, the lower surface web is angled more radically downwardly toward the jaw of a user to conform to a user's lower teeth.

The snorkel mouthpiece incorporates two frontal openings formed across the longitudinal orientation of the mouthpiece within which a user's frontal teeth can extend to engage the mouthpiece. These openings allow for a user's teeth to pass into the mouthpiece for ease of breathing and retaining the mouthpiece.

In an alternative embodiment which is deemed to be a preferred embodiment, the lower portion of the snorkel mouthpiece is split. The split opening allows for freedom of movement of the tongue of the user in a more facile manner. The split opening also allows for the flexibility of the base of the mouthpiece to retain the snorkel mouthpiece in place without covering completely the lower portion of the lower cavity near the jaw on the interior portion of the lower teeth.

The detachable snorkel mouthpiece incorporates a conduit having one or more interior grooves within the interior seating portion thereof. A tubular snorkel breathing extension having one or more exterior extension flanges engages the interior grooves. The end result is a firm and fixed fitting of the snorkel mouthpiece to the snorkel.

Alternately, the mouthpiece can also be integrally molded to a snorkel to provide for an improved snorkel and attendant mouthpiece. The net result of a detachable mouthpiece or an integrally molded mouthpiece is a snorkel with a highly comfortable and functional mouthpiece.

BRIEF DESCRIPTION OF THE DRAWINGS

The invention will be more clearly understood by reference to the description below taken in conjunction with the accompanying drawings wherein:

FIG. 7 shows a perspective view of an alternative and preferred embodiment of the snorkel mouthpiece of this invention.

FIG. 8 shows a bottom view looking upwardly from the view shown in FIG. 7.

FIG. 9 shows an end view of the snorkel mouthpiece as seen in the direction of lines 9—9 of FIG. 7.

FIG. 10 shows a perspective view of a snorkel with a purge valve having the mouthpiece of FIGS. 7, 8, and 9 attached thereto.

FIG. 11 shows as side view of the snorkel of FIG. 10.

DESCRIPTION OF THE PREFERRED EMBODIMENTS

Figure 1:
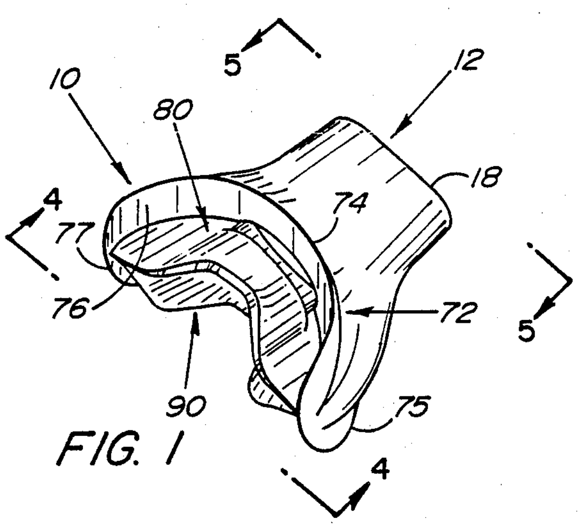
FIG. 1 shows a perspective view of the mouthpiece of a snorkel which incorporates this invention.

FIG. 1 shows an embodiment of the snorkel mouthpiece of this invention from an upper perspective view. The invention incorporates a mouthpiece configuration generally shown as mouthpiece area 10 which fits into a user's mouth. The mouthpiece flows into a generally rounded oblong portion 12.

Looking specifically at the mouthpiece portion 10 in FIGS. 1 through 6, it can be seen that a curved upper lip flange 72 is shown. The upper lip flange 72 is an area of the mouthpiece that is contoured to fit the upper interior portions of the lips. It comprises an upper exterior lip portion 74 and an upper interior lip portion 76. The upper interior lip portion 76 seats against the teeth of a user so as to accommodate the mouthpiece against a user's teeth. The upper exterior lip portion 74 seats against the inner portion of the lips so that it forms a seal when it is in a user's mouth.

Similarly, the mouthpiece also includes a lower lip flange 73. The lower lip flange 73 is contoured to fit the lower interior portions of the lips. It includes a lower exterior lip portion 75 and a lower interior lip portion 77. The lower interior lip portion 77 seats against the teeth of a user so as to accommodate the mouthpiece against a user's teeth. The lower exterior lip portion 75 seats against the inner portion of the lips so that it forms a seal when it is in a user's mouth.

The curved upper lip flange 72 and the curved lower lip flange 73 are generally flared to fit the space between a user's lips and teeth. This allows the unit to fit snugly against the upper and lower teeth and at the same time allow the lips comfortably to draw over onto the respective outer lip surfaces or portions 74 and 75. The two respective lip flanges 72 and 73 flow in a contoured manner with respect to the user's mouth so as to generally fill somewhat the area of the space between the inner portion of the user's lips and teeth.

Interiorly of the interior surface 76 of the mouthpiece portion 10 is an upper web or palate portion 80. The upper web 80 spans a portion of the palate of a user. The surface of the upper web 80 is configured to lie along a use's palate and generally conform to the interior portion of it. The upper web 80 includes a frontal portion or area corresponding to the front of the upper mouth of a user and two lateral portions corresponding to the upper lateral jaw regions of a user. The palate portion or upper web terminates in a frontal area at the interior surface 76 of the mouthpiece lip flange 72 in a frontal slot opening 82 which can be seen in the various figures and particularly FIGS. 2 and 6. The frontal slot opening 82 allows for the upper frontal teeth to project into the opening while at the same time allowing for the passage of air between the upper and lower set of teeth.

A lower web portion or interior jaw portion 90 is shown having a surface which is contoured to the interior surface of a user's jaw or lower teeth. The lower web 90 includes a frontal portion or area corresponding to the front of the lower mouth of a user and two lateral portions corresponding to the lower lateral jaw regions of a user. The lower web 90 is lesser in dimension as it extends inwardly to a user's mouth than the upper web 80. This serves to accommodate the more radical dropoff in the interior jaw region at the lower teeth. The lower web or jaw contacting web 90 has an interior surface 94 which is contoured to engage a user's lower teeth and interior jaw surfaces.

Figure 2:
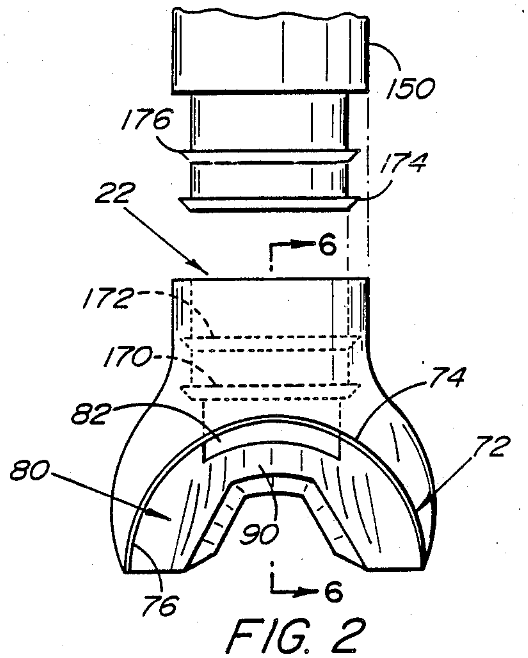
FIG. 2 shows a top plan view of the snorkel mouthpiece looking downwardly upon the showing of FIG. 1.
Figure 4:
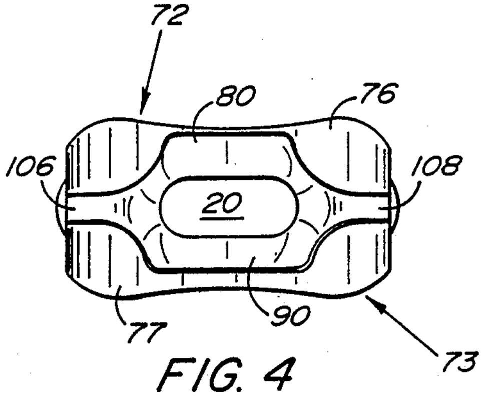
FIG. 4 shows an end view of the snorkel mouthpiece as seen in the direction of lines 4—4 of FIG. 1.
Figure 3:
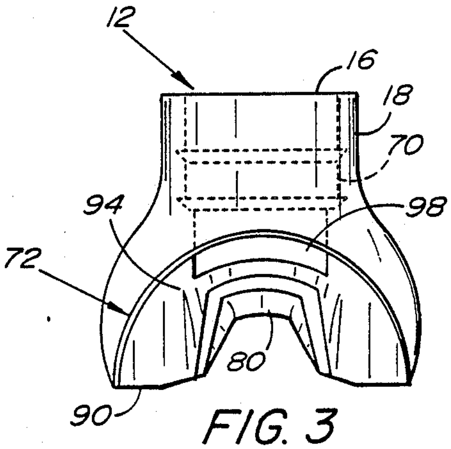
FIG. 3 shows a bottom plan view looking upwardly at the view shown in FIG. 1.
Figure 5:
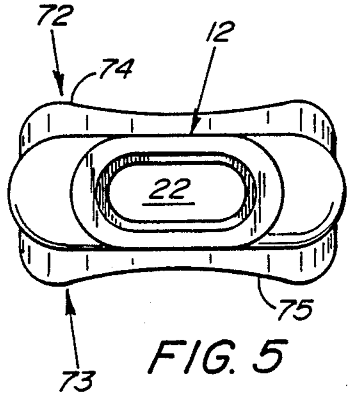
FIG. 5 shows an end view of the snorkel mouthpiece as seen in the direction of lines 5—5 of FIG. 1.

The lower web 90 also has a frontal slot opening 98 through which the front of the lower teeth can pass. The slot or opening 98 accommodates the teeth in the same manner as the slot 82 so that the respective upper and lower frontal teeth overlie each other as seen through the slots 82 and 98. This can be seen clearly in FIGS. 2 and 3 showing the fact that the slots 82 and 98 extend directly into each other and are aligned fundamentally in overlying relationship. The lower web 90 as can be seen in FIG. 3 underlies the upper web 80 to a significant degree and permits the radical dropoff in the manner as shown in the figures.

Looking more particularly at FIGS. 7 through 9, an alternative, and in many instances, preferred embodiment is shown. In looking at these figures, it can be seen that the outer surface 74 of the upper lip flange 72 is seen with the inner surface 76 which engages a user's teeth. Both are configured in the same manner as the prior showings. The upper web 80 is also shown which contacts the upper teeth and the palate. This upper web 80 also incorporates the slot or opening 82 as seen in the prior figures. The opening 82 allows for the frontal upper teeth to engage the mouthpiece while the surface of the upper web 80 extends across the interior palate of a user.

The lower web 90 has been shown with a split area 100. This split area 100 provides two respective rounded tabular portions 102 and 104. The tabular portions 102 and 104 are fundamentally tabs which extend downwardly along the inner jaw surface in a steep manner in the same manner as the slope shown by the lower web 90 in FIGS. 1 through 8. The split area 100 or space leaves the frontal area of a user's mouth free and allows for the tongue to move more freely while at the same time providing for a greater amount of air to be delivered into a user's mouth.

Both of the respective embodiments of FIGS. 1 through 7 and 7 through 9 cause the respective upper and lower webs 80 and 90 and tabular portions 102 and 104 to terminate in a thickened interfacial connecting web or flange. This is formed on either side as interconnecting web 106 and 108 of the two respective portions. These interconnecting webs 106 and 108 are of the same thickness and generally surround the interface between the respective upper and lower teeth. They extend from a region intermediate between the upper lip flange 72 and lower lip flange 73 and stop at the openings 82 and 98 respectively. However, it should be kept in mind that the showings of FIGS. 7 through 9 do not have the lower opening 98 inasmuch as the tabs 102 and 104 extend in such a manner as to be spaced by a gap or space 100 between the two tabs 102 and 104.

The space between tabs 102 and 104 can be provided in any suitable manner. Suffice it to say, in this particular embodiment, they are shown interfaced by rounded portions 112 and 114 of the tabs 102 and 104. This allows for a ready accommodation of the teeth and the passage of the tongue into the area while at the same time maintaining sufficient air passage.

The entire mouthpiece area 10 is such wherein the showing of FIGS. 7 through 9 provide for the dropoff at the surface of the tabs 102 and 104 to conform to the lower interior jaw area of a user. This angular declination along the lower interior jaw area overlying the inside of the lower teeth is of a steeper and more angular departure from the axial center line of the passage 22 than upper web 80. Thus, it can be relatively defined that the upper web or palate portion 80 is of a lesser angular inclination from the central axis of the mouthpiece conduit than the lower surface defined by tabs 102 and 104 or lower web 90. This varied angular inclination of the upper portion 80 and declination of the lower portion or web 90 or tabs 102 and 104 provide for the respective inclination and declination that maintains the mouthpiece in a configured manner against the palate of a user and the inner jawbone on the lower interior surface of the jaw and teeth.

The overall configuration allows for this orientation to be configured to retain the mouthpiece section 10 in a comfortable manner. This is true not only within the lips of a user as in the prior art but also within an interfacing orientation against the palate and lower jaw area.

This invention overcomes the foregoing problems by allowing for a contoured seating of the snorkel mouthpiece against the palate, the lower jaw area and interior tooth surfaces. It also accommodates the ability of the frontal teeth to be seated within the central axial passage 22 through the respective slot openings 82 and 98 or in the alternative the space 100 between tabs 102 and 104.

The snorkel mouthpiece of the invention is shown attached a snorkel in FIGS. 10 through 14. As shown in FIGS. 10 and 11 which display a snorkel having a purge valve 162, the snorkel is comprised of separate sections. The mouthpiece 10 is attached to a tubular breathing extension or section 164 from which it projects at a substantially right angle to the axial center of section 164. Also included in section 164 is a purge valve 162 which can be of any type desired, such as the mushroom valve type. The invention is not limited by the type of purge valve employed.

Attached to section 164 is a curved portion 166 which in turn is attached to an elongated tubular section 168. The sections 164, 166, and 168 constitute the breathing tube of the snorkel.

A preferred method for attachment of the mouthpiece to the snorkel is detailed in FIG. 2. As shown, the interior conduit 22 includes two parallel interior grooves 170 and 172 which lie normal to the center/axis of conduit 22. These are designed to slip fit over correspondingly sized parallel exterior flanges 174 and 176 located near the end of breathing tube extension 150. When joined together, the flange 174 fits within groove 170 and flange 176 fits into groove 172 to provide a smooth watertight seal.

Figure 6:
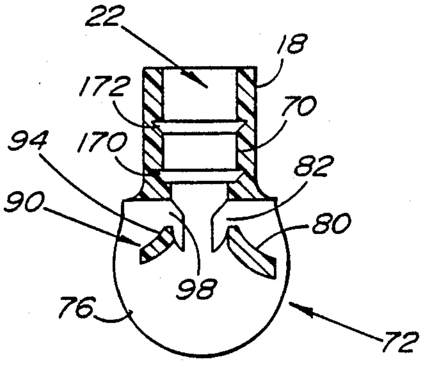
FIG. 6 shows a sectional view of the snorkel mouthpiece as sectioned along lines 6—6 of FIG. 2.

This can be seen in greater detail in FIGS. 2, 6, and 8.

Figure 14:
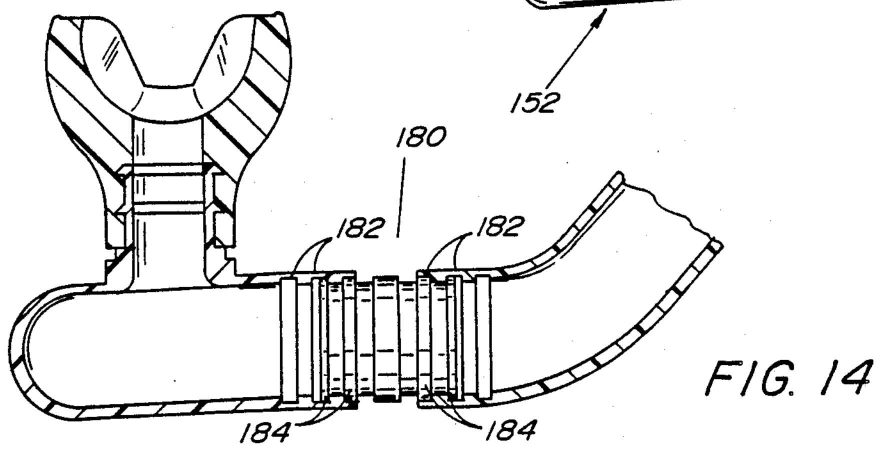
FIG. 14 shows a partially cut away section of the snorkel of FIG. 13.

With respect to the joining of the respective sections of the snorkel, any convenient means can be used. However, a preferred method includes the use of a double nipple 180 as shown in FIG. 14. The nipple 180 includes a plurality of exterior flanges 182 near each end which are configured to slip fit into correspondingly sized interior grooves 184 of the adjoining sections 164 and 166 and 166 and 168.

A particular advantage of using the nipple 180 to join the section 164 which connects the mouthpiece 10 to section 166 is that it is capable of rotation 360 degrees for individual adjustment of the exact angle of the mouthpiece 10 relative to the breathing tube sections 164, 166, and 168.

Figure 12:
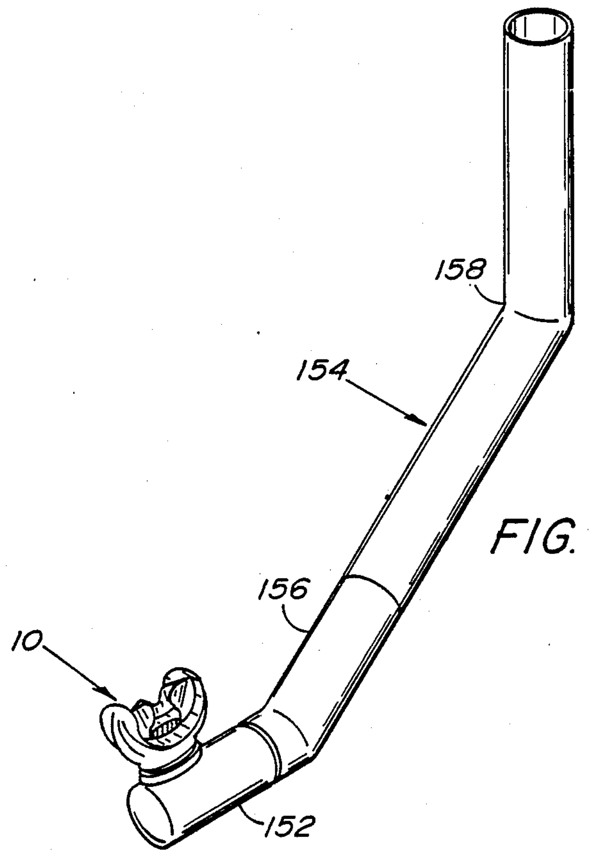
FIG. 12 shows a perspective view of a snorkel without a purge valve having the mouthpiece shown in FIGS. 1 through 6 attached thereto.
Figure 13:
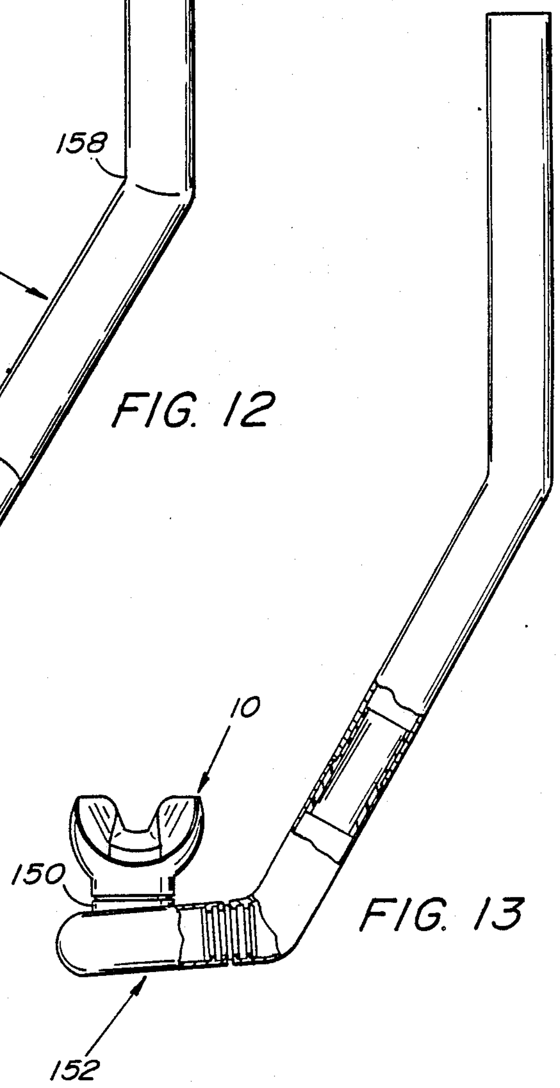
FIG. 13 shows a side view of the snorkel of FIG. 12 with a portion of the breathing tube cut away.

The snorkel of FIGS. 12 and 13 depicts a snorkel which is without a purge valve. It includes a section 152 having an upwardly projecting section 150 to which the mouthpiece 10 is attached in the same manner as for FIGS. 10 and 11. The remainder of the snorkel is similar to the snorkel with a purge valve. Thus, section 152 is connected to curved section 156 and elongated tubular section 158.

The mouthpiece can also be integrally molded with an elongated snorkel breathing tube. In such a case, the tube or conduit portion 12 is molded or formed to a snorkel. In this manner, a snorkel provided with the mouthpiece 10 functions to provide all the favorable features of the detachable snorkel mouthpiece.

Various modifications of the invention are contemplated which will be apparent to those skilled in the art and which can be made without departing from the spirit and scope of the invention. For example, while it is preferable to have the snorkel mouthpiece slip fit over the end of the snorkel breathing tube, the reverse can also be used. That is, the end of the breathing tube can be made to slip fit over the end of the mouthpiece.

As a consequence of the foregoing, this invention should be read broadly in light of the following claims.

I claim:

1. A mouthpiece for a snorkel wherein said snorkel has a breathing tube for conduction of breathing gas thereinto, a purge valve connected to said breathing tube for purging liquid from said breathing tube and means associated with said breathing tube for connection to said mouthpiece, said mouthpiece comprising:

conduit means adapted for connection to a breathing tube of a snorkel so that air carried through said breathing tube can pass in through said conduit means as well as exhaust from a user's mouth out through said conduit means;

a mouthpiece portion extending from said conduit means, said mouthpiece portion having a curved upper lip flange adapted generally for conforming to the interior region of a user's mouth between the upper teeth and the user's upper lips and a curved lower lip flange adapted generally for conforming to the interior region of a user's mouth between the user's lower teeth and the inner lower lips respectively;

said upper lip flange and said lower lip flange being joined to each other in a region intermediate between them;

each said upper lip flange and said lower lip flange including a frontal portion substantially coextensive with said conduit means and two opposed lateral portions extending from said frontal portion;

an upper interior web joined to and extending from said region intermediate between said upper and lower lip flanges, and being anatomically shaped for contact with at least part of the inside surfaces of at least the frontal upper teeth of a user and for extension at least partly in contact with a user's palate;

a lower web joined to and extending from the region intermediate between said upper and said lower lip flanges, said lower web being anatomically shaped for contact with at least a portion of the inside surfaces of the lower teeth of a user and for extension at least partly in contact with a user's interior lower jaw portion; and, each said upper web and said lower web including a frontal portion substantially coextensive with said conduit means and two opposed lateral portions extending from said frontal portion.

2. The mouthpiece as claimed in claim 1 further comprising:

an opening within said frontal portion of said upper web through which at least a portion of a user's upper teeth can extend.

3. The mouthpiece as claimed in claim 2 further comprising:

an opening within said frontal portion of said lower web through which at least a portion of a user's lower teeth can extend.

4. The mouthpiece as claimed in claim 3 wherein:

said conduit means includes inner grooves, and wherein said snorkel breathing tube has exterior flanges for seating within said inner grooves.

5. The mouthpiece as claimed in claim 1 further comprising:

an opening within said frontal portion of said lower web through which at least a portion of a user's lower teeth can extend.

6. The mouthpiece as claimed in claim 1 wherein:

said lower web is split and comprises two laterally opposed, spaced apart tabular members which are anatomically shaped for contact with at least a portion of the inside surfaces of the lower lateral teeth of a user, and for extension at least partially in contact with the inside lateral lower jaw region of a user, said tabular members being spaced from said conduit means to provide a passage therebetween for a user's tongue.

7. The mouthpiece as claimed in claim 6 wherein:

said interior upper and lower lip flange contact surfaces have a relatively smooth curvilinear surface to fit against a user's teeth.

8. In a snorkel provided with or without a purge valve and including a mouthpiece having a conduit in communication with an elongated breathing tube for the passage of breathing air through said conduit wherein the improvement comprises:

a mouthpiece section attached to said conduit having a pair of upper and lower lip flanges wherein said upper lip flange conforms to the interior region between a user's upper lips and a user's upper teeth and said lower lip flange conforms to the interior region between a user's lower lips and a user's lower teeth;

said upper lip flange and said lower lip flange being at least partly joined to each other in a region intermediate between them;

each said upper flange and said lower flange including a frontal portion substantially coextensive with said conduit means and two opposed lateral portions extending from said frontal portion;

an upper web which conforms generally to a user's palate which extends from and is substantially coextensive with said region between said upper and lower lip flanges; and, a lower web having a pair of spaced apart tab portions which conform generally to the interior teeth and jaw regions of a user and which extend from the outer lateral region intermediate between said upper and lower lip flanges for contact with the interior lateral lower teeth of a user and spaced apart sufficiently to allow the passage of gas into a user's mouth.

9. The snorkel as claimed in claim 8 wherein said mouthpiece further comprises:

an interfacial web portion which joins said upper web and said lower tabs against which the teeth of a user can be seated.

10. The snorkel as claimed in claim 9 wherein said mouthpiece further comprises:

an opening in the upper web through which the teeth of a user can extend.

11. The snorkel as claimed in claim 10 wherein:

said opening is in said frontal portion of said web for receiving at least a portion of a frontal portion of a user's teeth.

12. The snorkel as claimed in claim 11 wherein:

said conduit means is configured and adapted to extend over the elongated breathing tube of a snorkel and further comprising interior grooves within said conduit means and exterior flange means on said elongated breathing tube for seating within said inner grooves of said conduit means.

13. The combination of a snorkel provided with or without a purge valve and a breathing mouthpiece having an air passage therethrough for breathing which is connected to an elongated air tube of a snorkel for conduction of breathing air thereinto, wherein said mouthpiece comprises:

conduit means for connection to said elongated air tube of said snorkel;

upper and lower lip flanges extending from said conduit means in a curved arcuate configuration for conformation respectively to the area between the inner surface of the lips and the outer portion of the teeth of a user;

said upper lip flange and said lower lip flange being at least partly joined together in a region intermediate between them;

each said upper flange and said lower flange including a frontal portion substantially coextensive with said conduit means and two opposed lateral portions extending from said frontal portion;

an upper interior web which conforms generally to a user's palate which extends from and is substantially coextensive with said region between said upper and lower lip flanges;

at least a partial interior lower web extending from the region between said upper and lower lip flanges for contact with the interior lateral lower teeth of a user; and, each said upper web and said lower web including a frontal portion substantially coextensive with said conduit means and two opposed lateral portions extending away from said frontal portions.

14. The combination as claimed in claim 13 wherein: said lower web is formed of two spaced apart generally rounded tabs which conform generally to the interior lower teeth and jaw regions of a user and which extend from the outer lateral region between said upper and lower lip flanges for contact with the interior lateral lower teeth of a user.

15. The combination as claimed in claim 14 wherein: said upper web and lower tabs are joined in the region between said upper and lower lip flanges from which said upper web and lower tabs extend.

16. The combination as claimed in claim 15 wherein: said upper web has an opening through which the teeth of a user can extend.

17. The combination as claimed in claim 16 wherein: said opening in said upper web is within the frontal portion.

18. The combination as claimed in claim 13 further comprising:

an opening within the lower web through which the teeth of a user can extend.

19. The combination as claimed in claim 18 wherein: said upper web has an opening through which the teeth of a user can extend.

* * * * *